United States Patent [19]
Volpe

[11] Patent Number: 5,267,602
[45] Date of Patent: Dec. 7, 1993

[54] CASTING METALS

[75] Inventor: Costantino M. Volpe, New Fairfield, Conn.

[73] Assignee: J. F. Jelenko & Co., Armonk, N.Y.

[21] Appl. No.: 777,001

[22] Filed: Oct. 16, 1991

[51] Int. Cl.⁵ ............................................. B22D 18/06
[52] U.S. Cl. .................................... 164/284; 164/514; 164/256
[58] Field of Search ................. 164/284, 48, 492, 493, 164/494, 495, 113, 250.1, 512, 513, 514, 515, 119, 256, 306

[56] References Cited

U.S. PATENT DOCUMENTS

| | | | |
|---|---|---|---|
| 3,788,382 | 1/1974 | Daniel et al. | 164/250.1 |
| 4,254,817 | 3/1981 | Kidowaki et al. | 164/514 |
| 4,421,152 | 12/1983 | Shinkawa et al. | 164/250.1 |
| 4,504,591 | 3/1985 | Feagin | 164/361 |
| 4,538,671 | 9/1985 | Waterstrat | 164/514 |
| 4,580,617 | 4/1986 | Blechner et al. | 164/119 |
| 4,623,014 | 11/1986 | Faessler et al. | 164/519 |
| 4,762,165 | 8/1988 | Ogino et al. | 164/495 |
| 4,919,191 | 4/1990 | Brodersen | 164/495 |

Primary Examiner—Richard K. Seidel
Assistant Examiner—Erik R. Puknys

[57] ABSTRACT

Metal is cast by melting it in a crucible over a hole too small to enable gravity to make the molten metal pass through the hole, after which increased pressure is applied to the metal to drive it through the hole into a mold.

21 Claims, 2 Drawing Sheets

CASTING METALS

FIELD OF THE INVENTION

The invention relates to casting small metal parts, in particular titanium dental castings.

BACKGROUND OF THE INVENTION

It is known in the prior art to cast metals by heating in a crucible above a mold, and then discharging the molten metal through a hole into the mold, either by gravity alone, or by that supplemented with gas pressure or vacuum from the mold side, Kidowaki et al. U.S. Pat. No. 4,254,817, "Metal Casting Apparatus", granted Mar. 10, 1981; Waterstrat U.S. Pat. No. 4,538,671, "Arc Furnace for the Production of Small Investment Castings of Reactive or Refractory Metals such as Titanium", granted Sep. 3, 1985.

Investments with binding through a magnesium oxide ammonium phosphate reaction are known, as are such investments with fillers a mixture of zirconia and alumina.

SUMMARY OF THE INVENTION

I have discovered that casting of metals may be simply and reliably done by melting in a crucible above a mold, the crucible having a hole communicating with the mold, the hole being too small in diameter to allow, in view of surface tension and density, the melted metal to fall therethrough owing to gravity, and then driving the molten metal through the hole by the imposition of pressure thereabove.

I have discovered also that melting desirably occurs in a chamber into which an electrode extends for axial movement through a sealed bearing unit.

I have discovered too that a preferred investment composition, actionable at a lower temperature, may be provided by mixing with binder and filler materials a separate expansion material.

In preferred embodiments, the crucible is of low-oxygen, electronic grade, copper, which is split with a step along each half so that the two halves are pressed together in an axial (metal flow) direction along the steps, the hole extends axially with its flow cross-sectional area divided along a diameter so that half its cross-sectional area is in each of the crucible halves, and the crucible is in press-fit relation with a copper hearth, an outer annular area of the crucible being at a slightly greater angle to the horizontal (non-axial) than a mating inner annular area of the hearth.

In further preferred embodiments, the binder materials are a mixture of monoammonium phosphate and calcined magnesium oxide, the filler is a mixture of zirconia and alumina, and the expansion material is spodumene; and curing is by increasing temperature at 15° F. per minute to a temperature of at least 1900° F., which temperature is thereafter held for some time.

PREFERRED EMBODIMENT

The presently preferred embodiment is disclosed in the drawings, and is described in its structure and operation.

DRAWINGS

STRUCTURE

Figure 1:
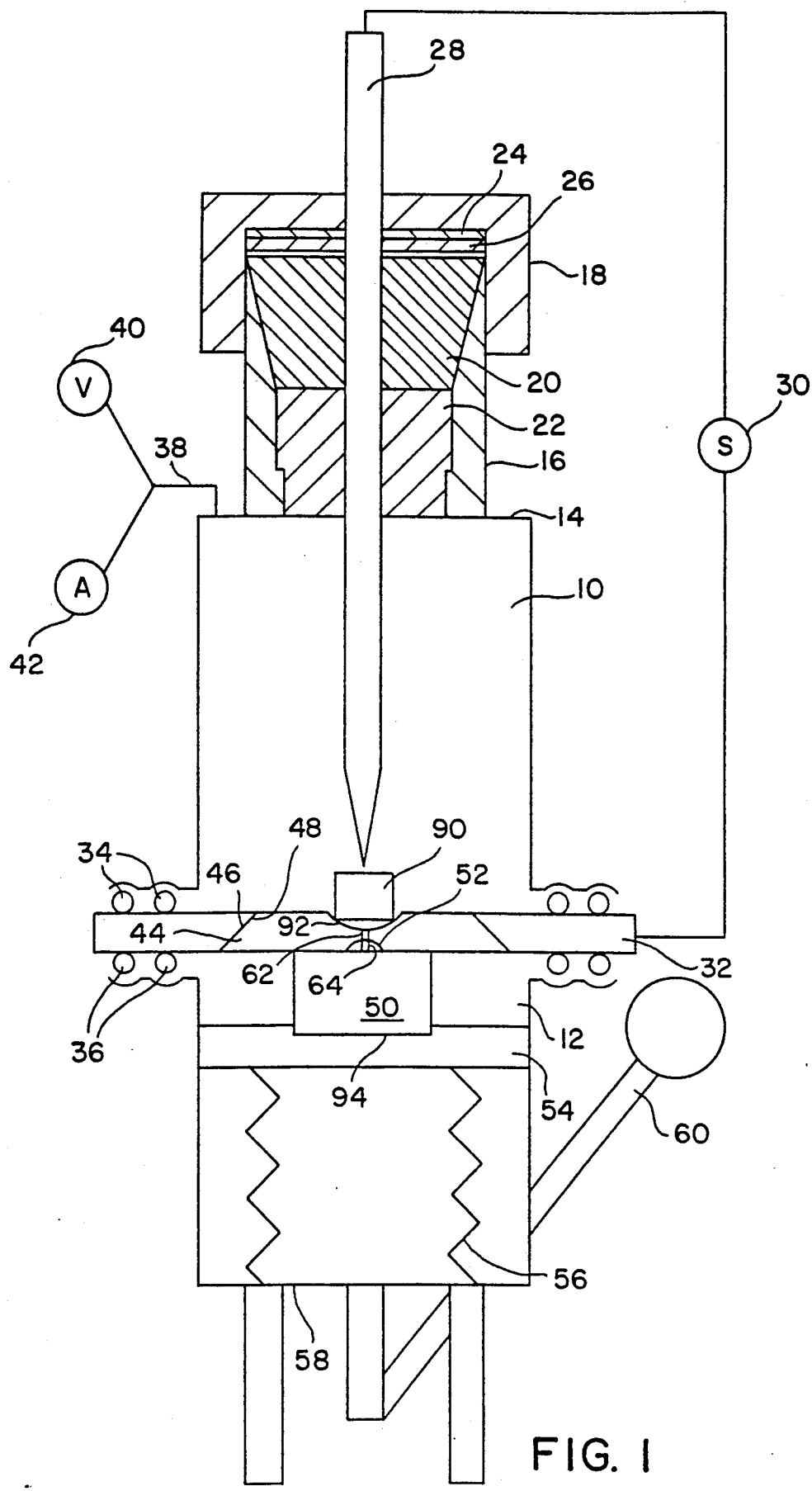
FIG. 1 is a somewhat diagrammatic overall view, in section, of the presently preferred embodiment of the invention.

There is shown in FIG. 1 an upper chamber 10 and a lower chamber 12.

Secured to the ⅛" thick stainless steel upper wall 14 of upper chamber 10, by welding (not shown), is stainless steel packing container 16, on which is screw-threadedly (threads not shown) mounted stainless steel follower 18. Secured in container 16 are silicone rubber bushing 20 and heat-resistant Teflon bushing 22. Above bushing 20 are nylon washers 24 and 26.

Extending through follower 18, washers 24 and 26, and bushings 20 and 22 is tungsten electrode 28, which is connected at its upper end to the positive side of high-frequency 175-ampere DC power supply 30, the negative side of which is connected to copper (low oxygen, electronic grade) hearth 32.

Electrode 28 may be adjusted up or down (by means not shown) upon loosening follower 18.

Hearth 32 is vacuum-sealed to chamber 10 through a pair of silicone rubber O-rings 34, and to chamber 12 through a pair of silicone rubber O-rings 36.

Connected to upper chamber 10 through line 38 are vacuum pump 40 and argon tank 42, with valve means (not shown) for switching therebetween.

Within and surrounded by hearth 32 is crucible 44, like hearth 32 of low-oxygen, electronic grade copper.

Hearth 32 and crucible 44 have almost-mating beveled surfaces 46, 48. Crucible 44 is held against hearth 32 by the force of springs 56, acting mediately through mold 50. Surface 46 is at 45° to the horizontal, and surface 48 at 45½° to the horizontal, the hearth and crucible mating in a vacuum-tight seal and electrical connection between said surfaces along annuli thereof toward the tops of the hearth and crucible.

Mold 50, from which protrudes the semispherical end of thermocouple insulator type pressed ceramic collar 52, is urged by plate 54 and three circumferentially equally spaced springs 56 (only two shown in FIG. 1), which are compressible through plate 58 by movement of handle 60, against a mating semispherical indentation in the bottom of crucible 44. Aligned holes 62 and 64, both 0.250 inches in diameter, extend respectively through crucible 44 and collar 52. This collar 52 is available of material under the designation 3F fish spine insulator from Arklay S. Richards Co. Inc., Newton Highlands, Mass. Hole 62 is defined by two semicylindrical half holes 62a, 62b, one in each of the crucible halves 44a, 44b. Hole 62 has a length in an axial direction of ⅛ inch.

Lips 80a, 80b extend each semicircumferentially around halves 44a, 44b, with spacings 82a, 82b defining annuli one-sixteenth inch in thickness (in an axial direction).

Figure 2:
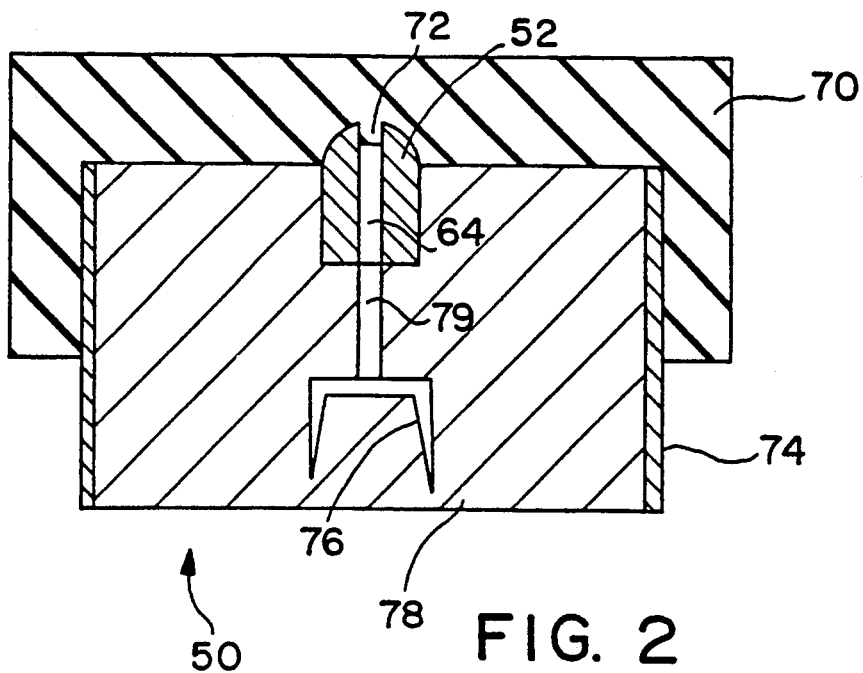
FIG. 2 is a sectional view, intermediately, of the mold portion of said embodiment.
Figure 3:
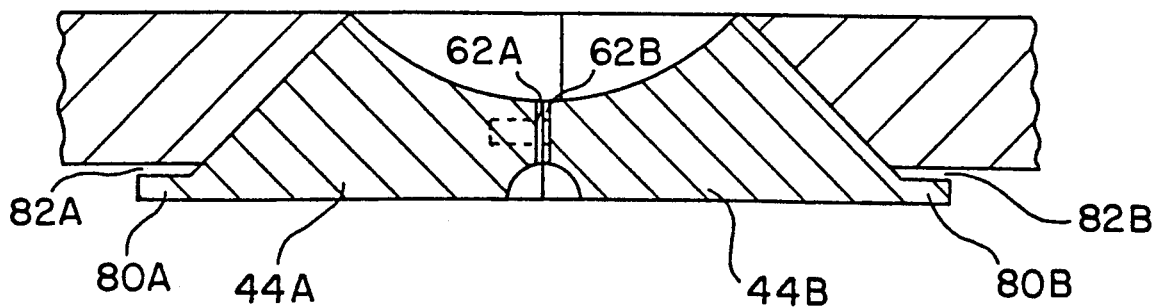
FIG. 3 is an enlarged view, in section, of the crucible and hearth (the latter partially broken away) of the preferred embodiment.

Mold 50 and collar 52 are shown in greater detail in FIG. 2, which shows also rubber former base 70 with nipple 72 used (in position upside down from FIG. 2) in making mold 50 (and thereafter removed before creating the FIG. 1 assembly), metal cylinder 74, mold cavity 76, and investment 78.

Investment 78 is a mixture of binder, filler, and expansion materials.

The binder materials constitute 12% by weight of investment 78. Half by weight (6% of the investment) is monoammonium phosphate, sold by Monsanto Chemical Co. under the designation Code 135; the other half is calcined magnesium oxide, suitably that sold by Premier Refractories and Chemicals under the designation Code DB 90.

The filler is 83% by weight of the investment 78. Of this, as percents of the investment, are: 20% zirconia (suitably that sold by Zircoa, Inc. as low silicon dioxide, 0.75 maximum, grade); 31.5%-100 mesh alumina (suitably as sold by Whittaker, Clark and Daniels under the designation No. 661); and 31.5%+325 mesh alumina (suitably as sold by the last-mentioned company under the designation No. 635).

The expansion material is lithium aluminosilicate, commonly known as spodumene, of particle size 44 microns, suitably available from Foote Minerals, King's Mountain, N.C., and constitutes the remaining 5% of the investment mixture.

OPERATION

To produce the mold 50, rubber former base 70 is oriented upside down from as shown in FIG. 2. Ceramic collar 52 is then mated with nipple 72, which aligns collar 52. A wax model corresponding in external configuration with the surfaces to be of mold form 76 is then attached, being joined through hole 64 of collar 52 by means of a wax sprue through holes 64 and 79.

The investment ingredients are mixed with one another and stirred with water in a vacuum, in the conventional manner, and then poured into tube 74 (positioned upside down from as shown in FIG. 2), into which extends the wax as described.

Former 70 is then removed, and the investment 78, after setting in about eight minutes and to full hardness in about an hour and a half, cured by "burnout" at a heating condition characterized by increasing temperature at 15° F. per minute to 1900° F., which temperature is then held for one hour.

The wax is, of course, removed (melted and then burned) during this step.

This investment provides low reactivity to titanium, good strength, and enough expansion to adequately deal with shrinkage both in certain of the investment components and in the cast titanium.

The mold and collar are then assembled to the crucible 44 and hearth 32 as shown in FIG. 1. Indentation 94 in plate 54 and collar 52 with the crucible lower indentation assure centering relative to each other of holes 62 and 64. Because of the indentation 92 atop crucible 44, and the coaxial relation of the indentation 92 and hole 62, balled molten titanium automatically rolls into position over hole 62, so that accurately locating ingot 90 relative to hole 62 is not necessary.

Use of springs 56 reduces the need for height accuracy in the mold-collar combination 50, 52.

Lips 80a, 80b by engaging hearth 32 if crucible halves 44a, 44b are not properly oriented with the hearth assure that the beveled surfaces go together properly.

The bevel surfaces 46, 48 provide added area for better electrical conduction.

Electrode 28 is then moved axially into contact with ingot 90, and follower 18 tightened down to produce a seal around the electrode by bushing 20.

The cooperating steps on container 16 and bushing 22 hold the latter against undue axial movement.

Bushing 20 is rubbery and flexible so that under urging of follower 18, in cooperation with the mating frustoconical surfaces of container 16 and bushing 20, it provides a seal around electrode 28. The washers 24 and 26 are non-conducting and have holes just large enough to permit free movement of electrode 28; washer 24 protects washer 26 from twisting, as follower 18 is turned.

Chamber 10 is then evacuated to two inches of mercury, following which it is filled with argon to a pressure of 28 inches of mercury. This sequence of evacuation to a pressure of two inches and introduction of argon to a pressure of 28 inches is then repeated. Finally, evacuation to two inches is done for a third time, further to reduce impurities present in chamber 10.

Argon is then introduced to a pressure of six inches of mercury.

An arc is then struck from electrode 28, in contact with 10 gram grade 2 titanium ingot 90, to crucible 44, melting the titanium, which, because of high surface tension and low density, stays on the upper concave surface 92 of the crucible, and does not drop through hole 62, but rather seals it off.

It is an advantage that there are thus no moving parts once the arc is struck.

Melting occurs in a few seconds, important both from an inherent time standpoint and to minimize reaction of titanium with any impurity present.

The mass of copper is large enough so that with its good thermal conductivity it is not melted despite the high temperature of molten titanium.

The relation of crucible 44, and its upper indentation and-hole 62, with collar 52, its hole 64, and mold 76 provide a clean short path for molten metal flow, minimizing waste and the quantity of metal needed for each casting.

Upper chamber 10 includes a porthole window (not shown) through which the condition of the ingot 90 and the molten ball melted from it may be visually observed, on the basis of which the time when the molten ball should be driven through holes 62, 64 may be concluded.

Although the titanium melts at 1668° F., its temperature is raised then to 1750° F., at which temperature a shimmering is observable.

Argon is then introduced, to a pressure of 1 atmosphere, driving the molten titanium through holes 62, 64 into mold 50. Because of the short ⅛" length of hole 62, there is not undue cooling of the molten titanium as it moves toward mold 50.

The copper of the crucible does not under all the circumstances unduly contaminate the molten titanium.

After casting and cooling, crucible and hearth are separated, and the two halves of the crucible separated, permitting easy removal of the casting. Because of the zirconium oxide in the investment, divesting and sandblasting clean of the casting are easy.

OTHER EMBODIMENTS

Metals other than titanium may be used, for example gold, silver, palladium, chromium, and alloys of these.

Other investment materials may be used.

Other crucible and hearth materials may be used.

The inert gas used to protect the titanium against reaction may be other than argon.

What is claimed is:
1. In combination,
a melting zone, arc heating means including an electrode mounted in said melting one, and a crucible in said melting zone, said crucible being of copper, and having therethrough a hole 0.250 inches in diameter, a casting zone including a dental casting mold, and pressuring means actable on said melting zone for driving molten metal through said hole into said casting zone.

2. The combination of claim 1 which includes in said casting zone a mold, said mold comprising a binder material, a filler material, and a separate expansion material.

3. The combination of claim 2 in which said separate expansion material is lithium aluminosilicate.

4. The combination of claim 3 in which said binder material is a mixture of monoammonium phosphate and calcined magnesium oxide.

5. The combination of claim 4 in which said filler is a mixture of zirconia and alumina.

6. The combination of claim 5 in which said expansion material has a particle size of 44 microns.

7. The combination of claim 1 which comprises also a hearth, said crucible being in thermal contact with said hearth therewithin.

8. The combination of claim 7 in which said crucible and said hearth are in annular relation.

9. In combination a melting zone, heating means mounted in said melting one, and a crucible in said melting zone, said crucible being of copper, and having therethrough a hole 0.250 inches in diameter, a casting zone, and pressurizing means actable on said melting zone for driving molten metal through said hole into said casting zone, which comprises also a hearth, said crucible being in thermal contact with said hearth therewithin, in which said crucible and said hearth are in annular relation, in which a beveled outer surface of said crucible engages a beveled inner surface of said hearth.

10. The combination of claim 9 in which said inner surface has a diameter decreasing in its axial direction toward said melting zone.

11. The combination of claim 10 in which said beveled outer surface is at a slightly less angle to axial than in said beveled inner surface.

12. The combination of claim 11 in which the angles referred to are respectively 44½ and 45°.

13. The combination of claim 1 in which said crucible is of copper.

14. In combination a melting zone, heating means mounted in said melting one, and a crucible in said melting zone, said crucible being of copper, and having therethrough a hole 0.250 inches in diameter, a casting zone, and pressuring means actable on said melting zone for driving molten metal through said hole into said casting zone, which includes a collar and a mold, said collar and said crucible having cooperating surfaces.

15. The combination of claim 14 in which said surfaces are semispherical.

16. The combination of claim 14 in which said collar is ceramic.

17. The combination of claim 1 in which said crucible is split.

18. The combination of claim 17 in which separate portions of said crucible abut in both transverse and axial directions other portions of said crucible.

19. The combination of claim 18 in which there are two semicircular said portions.

20. The combination of claim 19 in which dowel pins interconnect said portions.

21. The combination of claim 9 in which said crucible includes therearound, slightly spaced from said hearth, a lip for facilitating interengagement.

* * * * *